(12) United States Patent
Dolensky et al.

(10) Patent No.: US 7,780,769 B2
(45) Date of Patent: Aug. 24, 2010

(54) HIGH OUTPUT CONCENTRATOR

(75) Inventors: Joseph T. Dolensky, Kennesaw, GA (US); Robert J. Maddox, Jr., Cartersville, GA (US); Robert W. Murdoch, Acworth, GA (US)

(73) Assignee: Ric Investments, LLC, Wilmington, DE (US)

( * ) Notice: Subject to any disclaimer, the term of this patent is extended or adjusted under 35 U.S.C. 154(b) by 807 days.

(21) Appl. No.: 11/698,682

(22) Filed: Jan. 26, 2007

(65) Prior Publication Data

US 2007/0119305 A1   May 31, 2007

Related U.S. Application Data

(62) Division of application No. 10/935,733, filed on Sep. 7, 2004, now Pat. No. 7,429,289.

(51) Int. Cl.
*B01D 53/047* (2006.01)

(52) U.S. Cl. .......................................... 96/121; 96/130

(58) Field of Classification Search ..................... 95/96, 95/130; 96/108, 121, 130
See application file for complete search history.

(56) References Cited

U.S. PATENT DOCUMENTS

| 3,636,679 A | 1/1972 | Batta |
| 5,183,483 A | 2/1993 | Servido et al. |
| 5,997,617 A | 12/1999 | Czabala et al. |
| 6,551,384 B1 | 4/2003 | Ackley et al. |

*Primary Examiner*—Robert A Hopkins
(74) *Attorney, Agent, or Firm*—Michael W. Haas

(57) ABSTRACT

A multi-chamber canister for a pressure swing absorption system within a general housing assembly. The chambers include a first molecular sieve chamber for receiving a first molecular sieve for separating air from the ambient environment into a concentrated gas and at least a second molecular sieve chamber disposed within the housing assembly for receiving a second molecular sieve for separating air from the ambient environment into a concentrated gas component. Furthermore, a supply chamber is disposed within the housing for receiving air from the ambient environment and for communicating air to either first or second molecular sieve chambers.

5 Claims, 13 Drawing Sheets

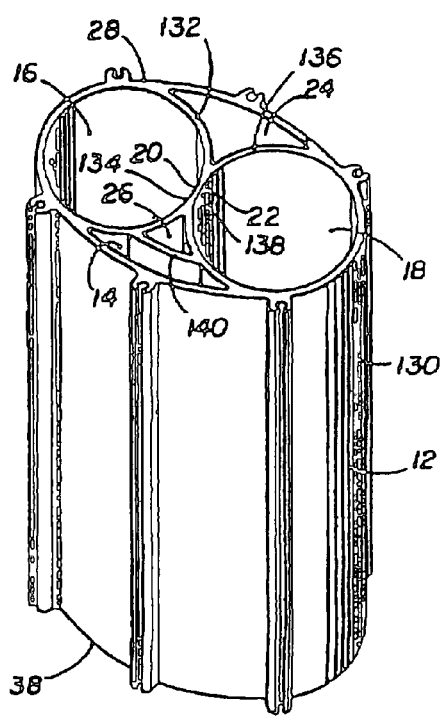
FIG 3
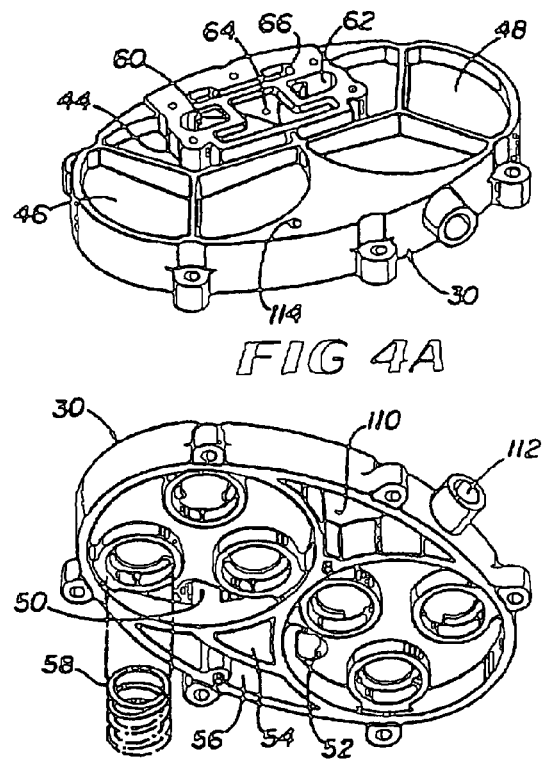
FIG 4A
FIG 4B

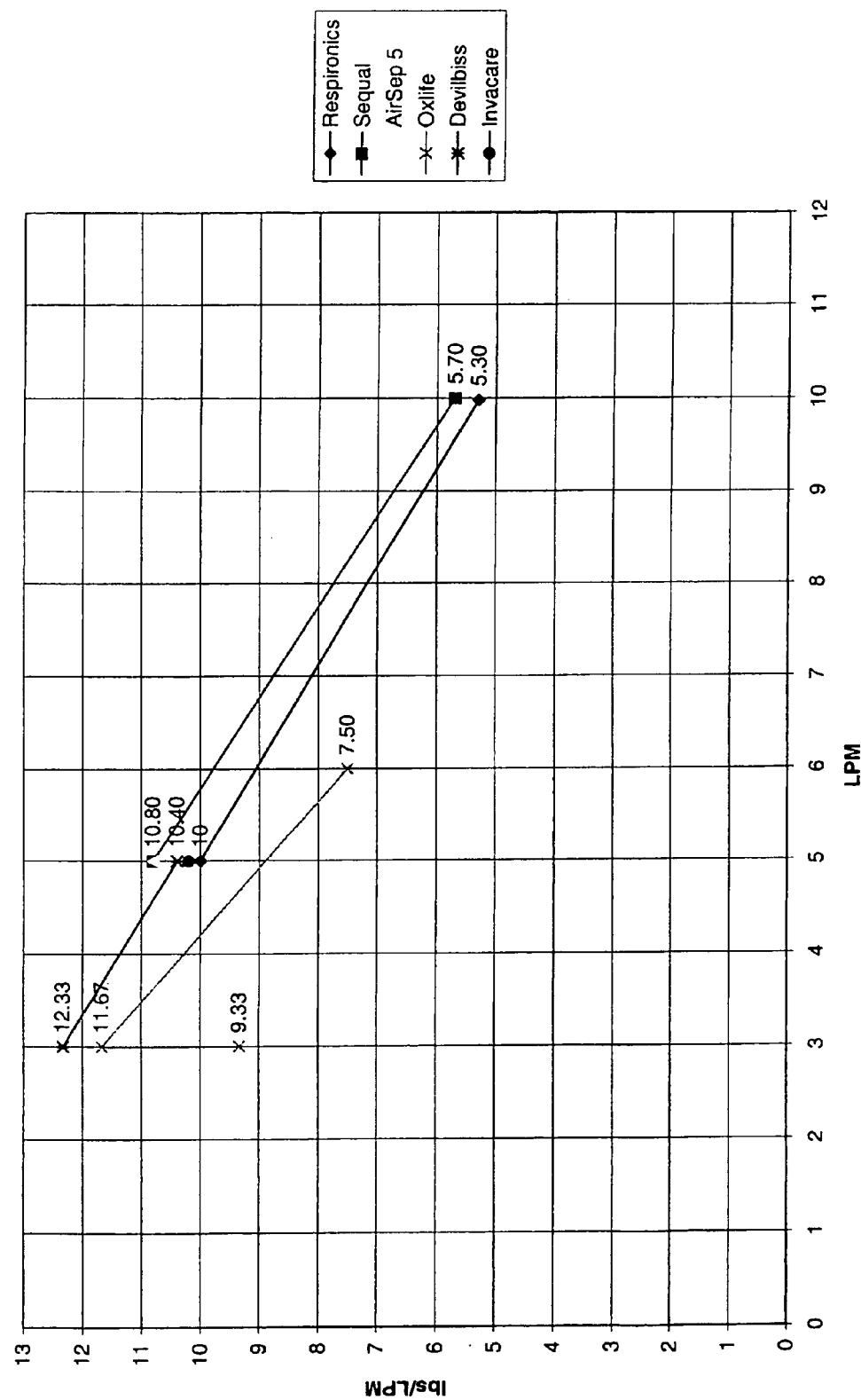

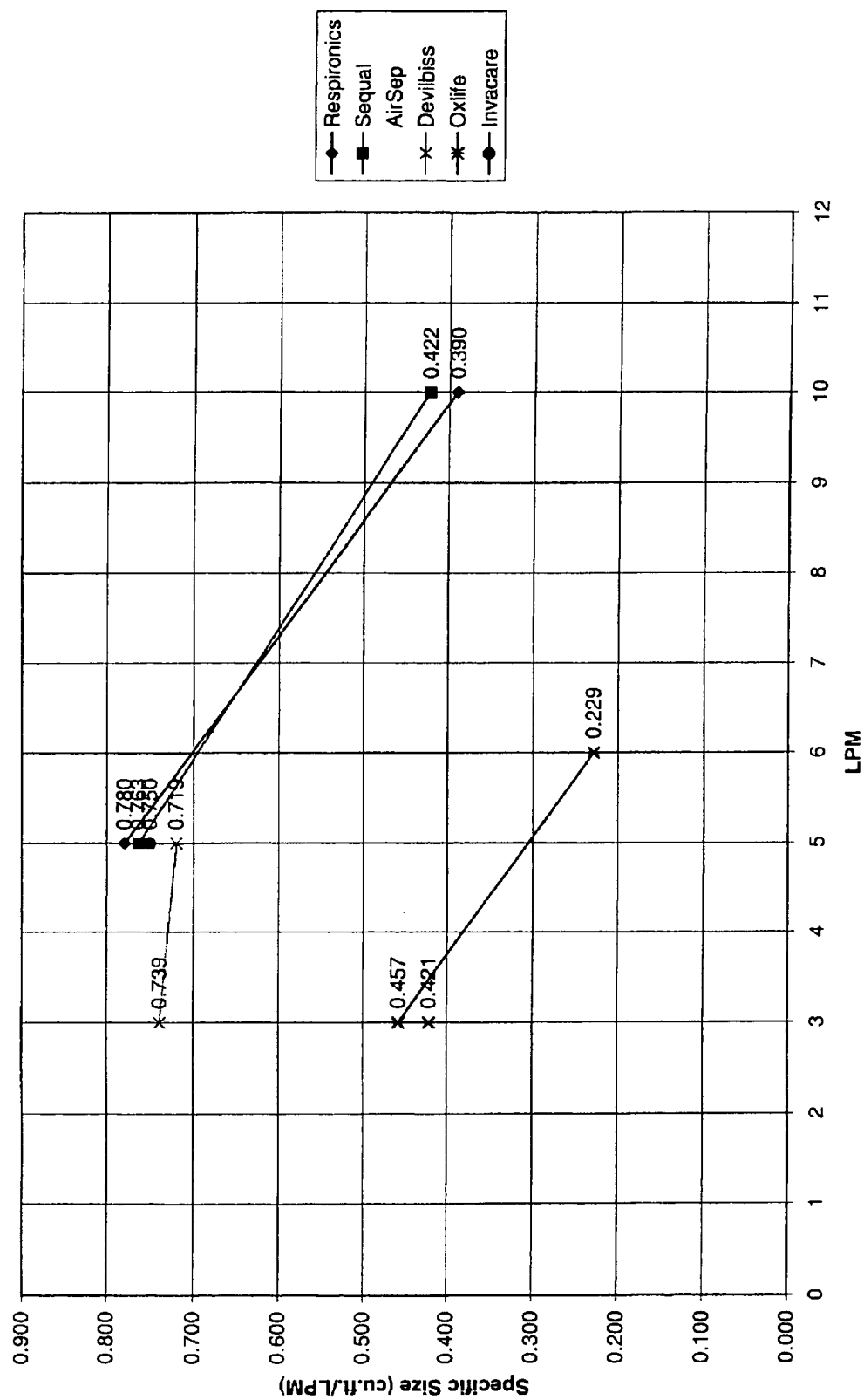

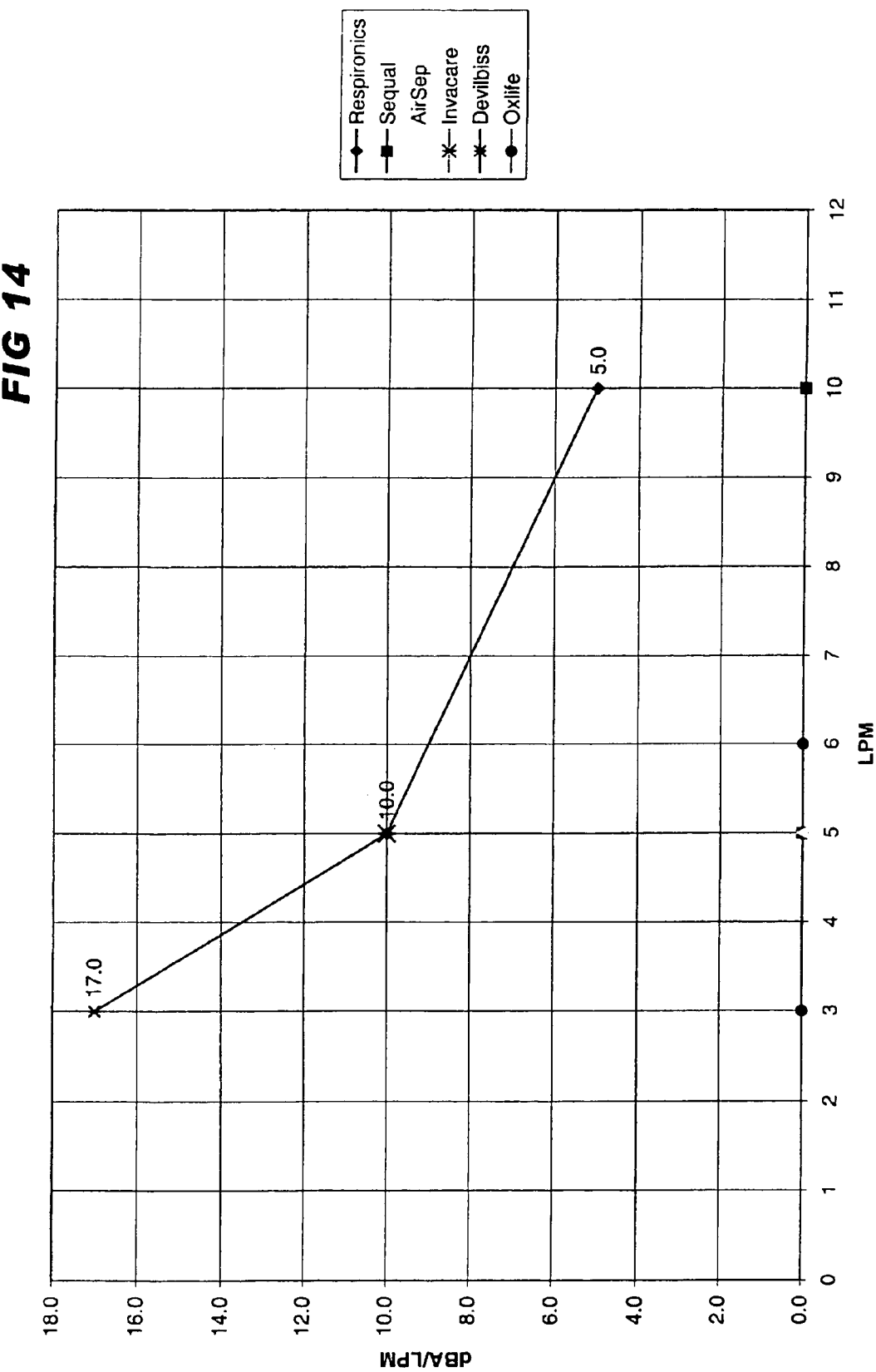

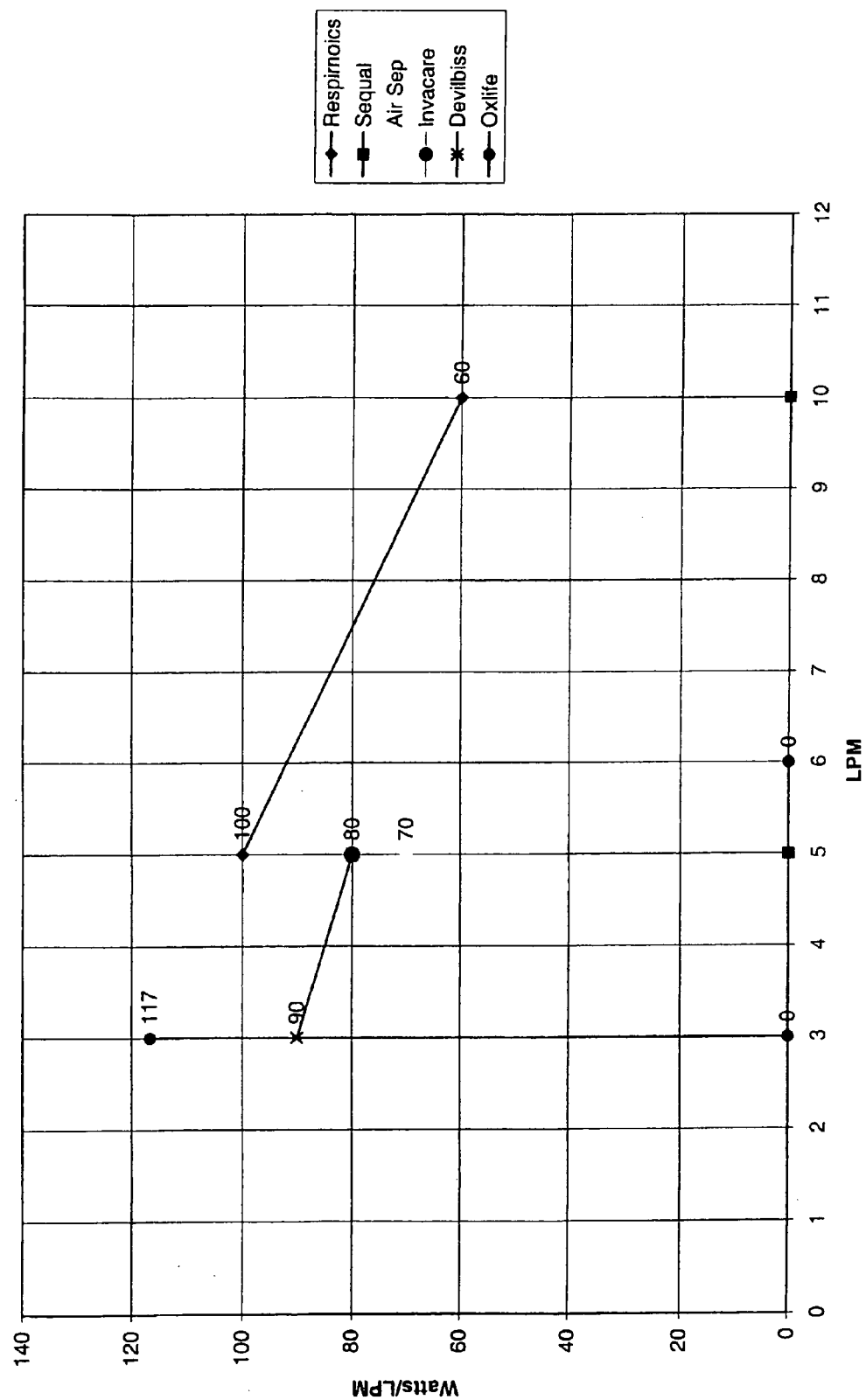

HIGH OUTPUT CONCENTRATOR

CROSS-REFERENCE TO RELATED APPLICATIONS

This application is a Divisional which claims priority under 35 U.S.C. §120/121 of U.S. patent application Ser. No. 10/935,733, filed Sep. 7, 2004.

BACKGROUND OF THE INVENTION

1. Field of the Invention

This invention relates to a pressure swing absorption chamber, and more particularly to an oxygen concentrator system having a multi-chamber canister for receiving compressed air from a compressor and directing the air through a series of chambers integral within a single assembly for producing concentrated oxygen in a pressure swing absorption system, which system provides 10 LPM at an oxygen concentration of at least 93%.

2. Description of the Related Art

Adsorption separation processes depend on the ability of certain solids to selectively adsorb one or more components from a gaseous mixture. In oxygen concentrators for patient use, the adsorption separation processes are usually fixed bed operations, including two main steps, the adsorption step and the desorption step.

Pressure Swing Adsorption (PSA) is a useful technique for separating components of gaseous mixtures in such medical uses. A gaseous mixture, typically ambient air, is fed into a chamber, where the species are separated, producing a stream with a high percentage of one component. Air contains many species, namely approximately 21% oxygen, 78% nitrogen, 0.9% argon and 0.1% other trace gases. PSA can be used to separate the oxygen from the inlet air, to supply the patient with higher concentrations of oxygen.

Generally, such species separation in the chamber is achieved by using a zeolite, or molecular sieve, which has a selective affinity for adsorbing a certain component in the mixture. Zeolites are natural or synthetically produced molecular sieves that have uniform pores or crystalline cavities. Chemical species small enough to fit into the zeolite's pores are adsorbed onto the surface of the zeolite material. How readily a species adsorbs onto the zeolite depends on the shape and size of the molecule compared to the shape and size of the pores in the zeolite pellet. A zeolite can adsorb a molecule of any diameter up to its own pore size.

Pressure Swing Adsorption relies on swings in pressure to cycle the chamber sequentially from selective adsorption to desorption. This swing can occur from high pressure to atmospheric pressure or from atmospheric pressure to vacuum. If the swing occurs from atmospheric pressure to vacuum, it is technically considered Vacuum Pressure Swing Adsorption (VPSA). It is well know to those of skill in the art the PSA and VPSA techniques for species separation are quite different, each technique with its own attendant benefits and deficiencies.

A typical pressure swing absorption system is an oxygen concentrator that separates the oxygen from air for subsequent inhalation by a patient. Conventional systems provide 5 liters per minute (LPM). Such oxygen concentrators include a plurality of molecular sieve beds for separating the gas into an oxygen and a nitrogen fraction whereby the oxygen is subsequently provided to a patient while the nitrogen is retained in the sieve bed and subsequently purged. These oxygen concentrators include several components such as an air compressor, two three-way air valves, multiple canisters each housing a separate molecular sieve and a product reservoir tank. Such structures require extensive valving and plumbing which affects the efficiency and costs of these systems.

U.S. Pat. No. 5,997,617 to Czabala et al. discloses an improvement in the art of 5 LPM pressure swing absorption system that incorporates a multi-chamber canister assembly for improving both the efficiency of the system, and the cost of the system. The assembly minimizes the temperature difference between molecular sieves due to their location within the canister, and provides a system wherein multiple operations of the pressure swing absorption system are incorporated within a single housing assembly.

The Czabala et al. PSA system includes a multi-chamber canister for a pressure swing absorption system which includes at least three chambers. The canister includes a housing of a general length. A first molecular sieve chamber is disposed within the housing for receiving a first molecular sieve for separating air from the ambient environment into a concentrated gas component. At least a second molecular sieve-chamber is also disposed within the housing for receiving a second molecular sieve for separating air from the ambient environment into a concentrated gas component. A supply chamber is disposed within the housing for receiving air from the ambient environment and for communicating the air to either the first or second molecular sieve chamber.

When those of skill in the art approach the problem of "scaling-up" a Czabala et al.—like device to deliver in the range of 10 LPM, they have, prior to the present invention, simply attempted to design such systems with double the sieve material, and double the air flow, to provide double the resulting 5 LPM of oxygen. Yet, the additional sieve material weight and volume in such an approach results in a device of a size and weight that is disadvantageous not only to the market, but to the patient as well in view of price, noise, size, weight and power consumption.

An example of such a device is the INTEGRA$_{TEN}$™ by SeQual. This concentrator is marketed as a 10 LPM, but suffers from basically a doubling of SeQual's 5 LPM unit. Further, it utilizes at least twelve individual chambers, sequentially directing the flow of compressed air to a group of four sieve beds (adsorption), while at the same time another four beds are purged into the atmosphere through the valve (desorption). The remaining four of the twelve beds are interconnected through the valve to equalize pressure as the sieve beds sequentially transition between adsorption and desorption. Thus, not only does the unit have an overabundance of chambers, it is nearly twice the weight, nearly twice the size, and uses nearly twice the adsorbent material of the 5 LPM device to provide up to 10 LPM. Further, the oxygen concentration from ½ to 7 LPM is only 93.5% (±1.5%), and from 7 to 10 LPM is only 92% (±3%).

The INTEGRA$_{TEN}$™ has some disadvantageous specific performance ratios. For example, the INTEGRA$_{TEN}$™ is 4.22 ft$^3$, and thus has a specific unit size per LPM=0.422 ft$^3$/LBM when providing 10 LPM. Further, this unit has a weight of 57 lbs., and thus has a specific unit weight per LPM=5.7 lbs./LBM when providing 10 LPM.

Thus, while the Czabala et al. system is beneficial, and is efficient in the 5 LPM range of operation, and the INTEGRA$_{TEN}$™ by SeQual provides up to 10 LPM in a scaled-up version of their 5 LPM unit, it would be desirable to provide a PSA system that could deliver high output in the range of 10 LPM in a two chamber system, and deliver a reliable oxygen concentration of 93% or more at 10 LPM, all in a system that has similar weight, size, sound level and power consumption characteristics as the Czabala et al. system. It is to such an oxygen concentration system that the present invention is primarily directed.

SUMMARY OF THE INVENTION

Briefly described, in its preferred form, the present system is a relatively light weight, small size, low sound level, low power consumption PSA oxygen concentrator with an output in the range of 10 LPM. The system is an improvement over the prior art, and can provide the beneficial characteristics of a 10 LPM system in a compact device with its use of, among other improvements, a highly adsorbent molecular sieve, and a high flow compressor that is matched to the 10 LPM output and the higher performance molecular sieve.

The present invention, illustrated under the column of TABLE 1 labeled "Respironics 10" has many beneficial performance ratios over the conventional 5 LPM devices, and the 10 LPM device of INTEGRA$_{TEN}$™ by SeQual, under the column of TABLE1 labeled "Sequal 10".

It is clear from the concentrator comparisons of TABLE 1 that the present invention provides superior performance over the conventional devices, and embodies specific performance ratios that distinguish it from the prior art. Many of the identified concentrators of TABLE 1 while perhaps exhibiting some beneficial ratios, are in fact less than 10 LPM systems, as distinguishable from the present system.

Namely, the present invention is an absorption system for separating air into a concentrated gas component, including an air supply, a compressor for receiving and compressing the air supply, providing a compressed air supply, molecular sieve material for separating the compressed air supply into a concentrated gas component; and an outlet delivering at least 10 liters per minute (LPM) of concentrated gas component from the molecular sieve material.

The present 10 LPM system preferably has at least one of the following beneficial performance ratios:

a specific total weight per LPM<5.7 lbs./LBM;

a specific total molecular sieve material weight per LPM≦1 lbs./LBM;

a specific volume per LPM≦0.422 ft$^3$/LBM;

a specific sound level per LPM≦10 dBA/LBM; and/or a specific power level per LPM≦120 W/LBM.

In one preferred embodiment, the present invention is a pressure swing absorption system having five or less molecular sieve beds for separating air into an oxygen and a nitrogen fraction whereby the oxygen is subsequently provided to a patient while the nitrogen is retained in the sieve bed and subsequently purged, wherein the recovery rate is greater than approximately 30% (O$_2$ $_{OUT}$/O$_2$ $_{IN}$). In another preferred embodiment, the system has two beds.

In another preferred embodiment, the present invention comprises a maintenance free SMC® "sure cycle" valve, designed specifically for the present invention, has an Optional Oxygen Percentage Indicator (OPI®) that ultrasonically measures oxygen output as a purity indication, has protective tubing neatly guarding the electrical wires and tubing—that is a double fault against electric shock, has an integrated sieve canister that reduces tubing connections to enhance bed life, has a twin head compressor (higher stroke for more airflow through sieve beds), has a smooth bottom making cleaning the cabinet easier, and has highly durable casters designed to withstand rigorous usage.

Preferred specifications of the present invention include:

| | |
|---|---|
| Flow Rate | 10 LPM in 1 liter increments |
| Electrical Requirements | 120 V/60 Hz (±10%) |
| Oxygen Percentage Indicator | Green Light Normal greater than 82% |
| | Yellow Light between 70-82% |
| | Red Light Less than 70% |
| Oxygen Concentration | 92 ± 4% @ 8-10 LPM |
| | 94 ± 2% @ 3-7 LPM |
| | 92 ± 4% @ 1-2 LPM |
| Weight | 53 ± .5 lbs |
| Dimensions | 27" × 19" × 13" |
| Storage/transport Temperature | −30 to 160° F. |
| Operating Temperature | 55-90° F. |
| Storage/transport Humidity | Up to 95%, non-condensing |
| Operating Pressure | 10-30 psig |
| Alarm Indicators | High system pressure |
| | Low system pressure |
| | Power failure |
| | Low oxygen level |
| | No oxygen flow |

These and other objects, features and advantages of the present invention will become more apparent upon reading the following specification in conjunction with the accompanying drawing figures.

BRIEF DESCRIPTION OF THE DRAWINGS

FIG. 3 is a perspective view of a multi-chamber canister for use in a pressure swing absorption system according to an embodiment of the present invention.

FIG. 4a is a perspective view of a top cover for communicating fluid flow within a multi-chamber canister for use in a pressure swing absorption system according to an embodiment of the present invention.

FIG. 4b is a perspective view of a top cover for communicating fluid flow within a multi-chamber canister for use in a pressure swing absorption system according to an embodiment of the present invention.

FIG. 12 is a graph of the specific unit weight versus LPM of the concentrators of TABLE 1.

FIG. 13 is a graph of the specific size versus LPM of the concentrators of TABLE 1.

FIG. 14 is a graph of the specific sound level versus LPM of the concentrators of TABLE 1.

FIG. 15 is a graph of the specific power versus LPM of the concentrators of TABLE 1.

DETAILED DESCRIPTION OF THE EXEMPLARY EMBODIMENTS

Figure 1:
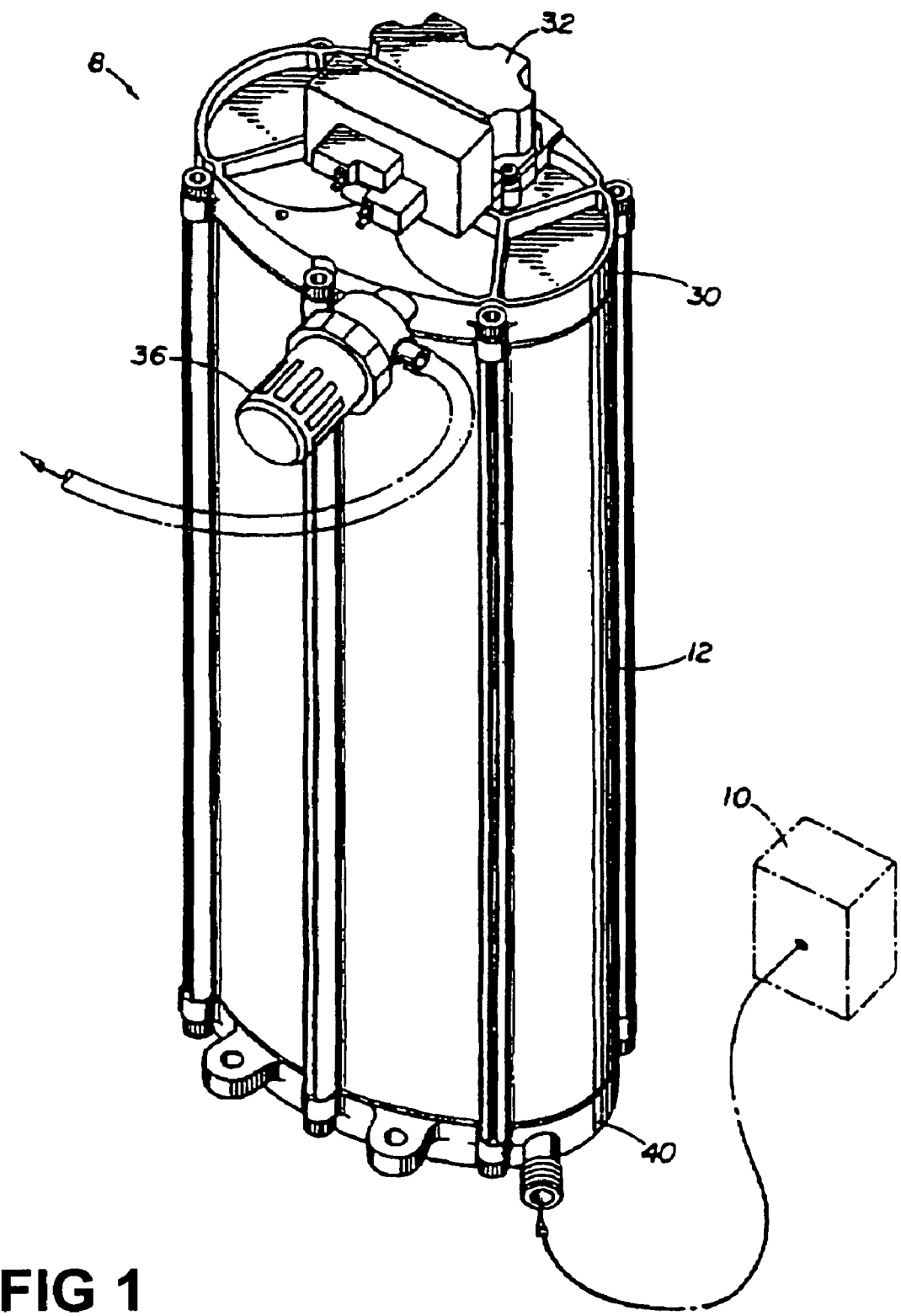
FIG. 1 is a perspective view of a pressure swing absorption system according to an embodiment of the present invention.

Referring now in detail to the drawing figures, wherein like reference numerals represent like parts throughout the several views, FIGS. 1 and 3 illustrate a pressure swing absorption system 8 including a compressor 10 having an inlet for receiving air from the ambient environment. Compressor 10 compresses the air and provides the pressurized air to multi-chamber canister 12. In the preferred embodiment, the present pressure swing absorption system 8 fractionalizes oxygen from the air in an oxygen concentration system. The operation and design of oxygen concentration systems are described in U.S. Pat. Nos. 5,183,483 and 5,997,617, both of which are hereby incorporated by reference.

Compressor 10 is preferably a high flow compressor that is oiless, and cooperative with the high output range of 10 LPM. A twin-head compressor can be used.

Multi-chamber canister 12 includes multiple chambers for producing concentrated oxygen from pressurized air. Canister 12 is preferably a cylindrical elongated housing providing sufficient volume for the respective chambers. In the preferred embodiment, canister 12 is a single extrusion, but can comprise of separate housings interconnected for forming a canister assembly. Supply chamber 14 receives the pressurized air from the compressor for delivery to the molecular sieves. First molecular sieve chamber 16 is located adjacent to second molecular sieve chamber 18 which house zeolite or other suitable material for fractionating air into oxygen and a waste product gas such as nitrogen.

Zeolites are highly crystalline alumino-silicate frameworks comprising $[SiO_4]^{4-}$ and $[AlO_4]^{5-}$ tetrahedral units. T atoms (Si, Al) are joined by an oxygen bridges. Introduction of an overall negative surface charge requires counter ions e.g. $Na^+$, $K^+$, and $Ca^{2+}$. The zeolite crystals contain water, and as the water is driven off by heating, there is no discernible collapse of the framework structure. This leads to a highly crystalline, microporous adsorbent that has an internal structure which can be easily tailored to adsorb any number of species.

Zeolites have beneficial molecular sieving properties. The pore size distribution can be modified, enabling the zeolite to be used as a so-called molecular sieve. Molecules which are too large to diffuse into the pores are excluded, whereas molecules which have a kinetic diameter smaller than the pore size, diffuse into the pores, adsorb and under certain conditions are capable of undergoing catalytic reactions. An example of this is in the sieving of straight and branched chained hydrocarbons to increase the octane number of gasoline.

In order to enable the present system to deliver a relatively light weight, small size, low sound level, low power consumption PSA oxygen concentrator with an output in the range of 10 LPM, a highly adsorbent molecular sieve preferably is employed. SILIPORITE® Molecular Sieves are mineral synthetic products (zeolites) with remarkable selective adsorption properties, and are an example of a preferable material for fractionating air into oxygen and a waste product gas such as nitrogen for use with the present system.

ATOFINA Chemicals, Inc. distributes and provides technical services for SILIPORITE® Molecular Sieves for its sister company, CECA S.A. Both Nitroxy 5 and Nitroxy 51 in the SILIPORITE® line are beneficial.

First molecular sieve chamber 16 and second molecular sieve chamber 18 have abutting walls 20 and 22 to maintain a constant temperature between the chambers which reduces the swing in oxygen concentration between the two chambers. Product chamber 24 is in fluid communication with both first molecular sieve chamber 16 and second molecular sieve chamber 18 for receiving and storing concentrated oxygen produced by the respective sieves. Exhaust chamber 26 is in fluid communication with both first and second molecular sieve chambers 16 and 18 and receives the waste product gas which has been purged from a respective molecular sieve. Each of these chambers extends along the length of multi-chamber canister 12.

As shown in FIG. 3, multi-chamber canister 12 is preferably designed as a single extruded unit having a single canister housing wall 130 with all of the respective chambers defined within housing wall 130. First molecular sieve chamber 16 is defined by first molecular sieve chamber partition 132 interfacing with canister housing wall 130. First molecular sieve chamber partition 132 has a first end and a second end which interface with canister wall 130. An intermediary portion of first molecular sieve chamber partition 134 is offset from canister wall 130 to assist in defining first molecular sieve chamber 16. Like first molecular sieve chamber 16, second molecular sieve chamber 18 is defined by second molecular sieve chamber partition 136 interfacing with canister housing wall 130. Second molecular sieve chamber partition 136 has a first end and a second end which interface with canister wall 130. An intermediary portion of second molecular sieve chamber partition 138 is offset from canister wall 130 to assist in defining second molecular sieve chamber 18. In the preferred embodiment, intermediary portions 134 and 138 respectively abut each other to maintain a consistent temperature between the two molecular sieve beds.

As further shown in FIG. 3, supply chamber 14 is defined within multi-chamber canister 12 by supply chamber partition 140 being offset from canister housing wall 130. Exhaust chamber 26 can be defined by its own exhaust chamber partition, or as shown in FIG. 3 as one embodiment, defined by the offsets of first and second molecular sieve partitions 132 and 136 in combination with the offset of supply chamber partition 140. Likewise, product chamber 24 can be defined by its own product chamber partition being offset from canister housing wall 130, or as one embodiment, defined by the offsets of first and second molecular sieve partitions 132 and 136 in combination with an offset with canister housing wall 130. Each of the respective partitions extends along the length of multi-chamber canister 12. It is understood that several chamber configurations can be had within the housing and that a particular chamber can be defined either by its own particular partition or as an offset between two other partitions.

Figure 2:
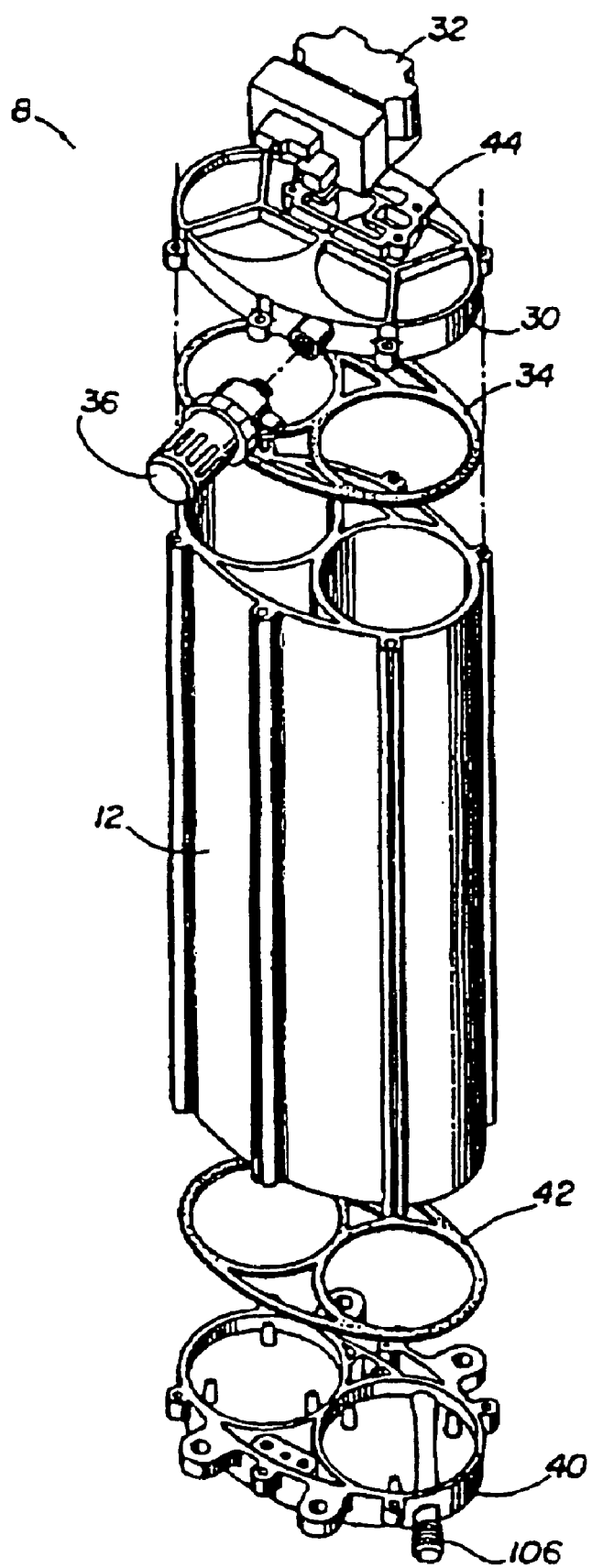
FIG. 2 is an exploded view of a pressure swing absorption system according to an embodiment of the present invention.

An exploded view of the multi-chamber canister assembly is shown in FIG. 2. Top portion 28 of multi-chamber canister 12 carries a top cover 30. Top cover 30 encloses the top portion of the respective chambers of multi-chamber canister 12 and includes a plurality of orifices enabling fluid flow between the respective chambers which will be described in more detail hereinafter. Valve 32 directs the communication of fluid flow between the orifices of top cover 30 and the respective chambers of multi-chamber canister 12. Top cover seal 34 seals the connection between top cover 30 and multi-chamber canister 12. Pressure regulator 36 regulates the pressure of concentrated oxygen delivered from product chamber 24 to a patient. The bottom portion 38 of multi-chamber canister 12 carries bottom cover 40. Bottom cover 40 encloses the bottom of the respective chambers of multi-chamber canister 12 and provides for fluid communication between the respective chambers as will be described in more detail hereinafter. Bottom cover seal 42 seals the connection between bottom cover 40 and multi-chamber canister 12.

Top cover 30 is shown in more detail in FIGS. 4a and 4b and includes valve seat 44. Top cover 30 includes first molecular sieve cover plenum 46 and second molecular sieve cover plenum 48. Disposed within first molecular sieve cover plenum 46 at a point which aligns with valve seat 44 is first molecular sieve inlet port 50 which will provide fluid communication with first molecular sieve 16. Disposed within second molecular sieve cover plenum 48 at a point which aligns with valve seat 44 is second molecular sieve inlet port 52 which will provide fluid communication with second molecular sieve 18. Top cover 30 also includes exhaust port 54 which communicates with exhaust chamber 26 to permit venting of waste product gas from the system. Furthermore, disposed within top cover 30 is supply port 56 which communicates with supply chamber 14. Springs 58 are carried by top cover 30 for maintaining the molecular sieve zeolite material in place within the respective molecular sieve chambers.

Valve seat 44 includes various ports which correspond with the aforementioned ports of top cover 30 for communicating fluid flow throughout the pressure swing absorption cycle. Valve seat first molecular sieve port 60 communicates with first molecular sieve port 50, valve seat second molecular sieve port 62 communicates with second molecular sieve port 52, valve seat exhaust port 64 communicates with exhaust port 54 and valve seat supply port 66 communicates with supply port 56. Valve 32 is carried by valve seat 44 for directing fluid flow between the respective ports during operation of the pressure swing absorption system.

Figure 5:
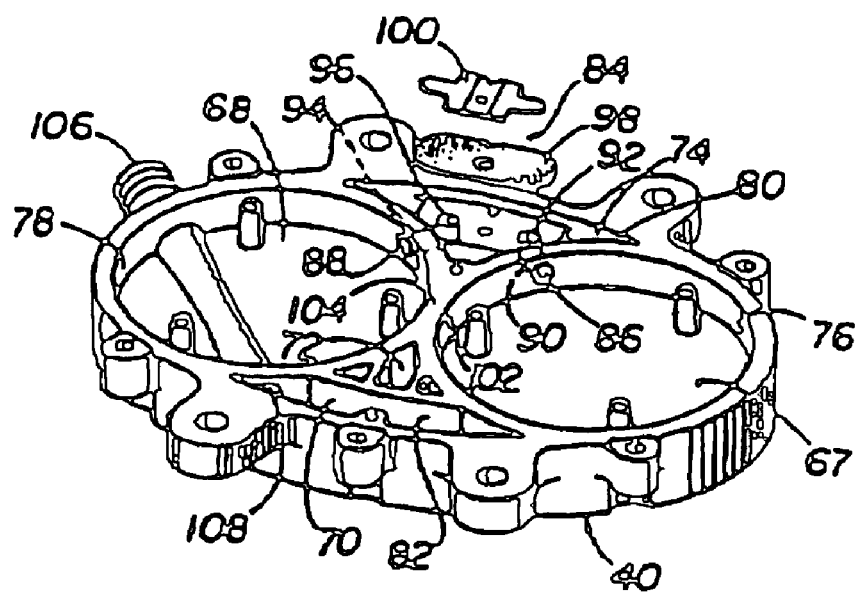
FIG. 5 is a perspective view of a bottom cover for communicating fluid flow within a multi-chamber canister for use in a pressure swing absorption system according to an embodiment of the present invention.

FIG. 5 illustrates bottom cover 40 which controls flow between the respective molecular sieves 16 and 18 during the purging cycle and also controls the delivery of product gas from the respective molecular sieves to product chamber 24. Bottom cover 40 includes first molecular sieve bottom cover plenum 67, second molecular sieve bottom cover plenum 68, supply chamber bottom plenum 70, exhaust chamber outlet port 72, and product tank bottom plenum 74. Bottom cover 40 includes cavities such that the respective chambers are defined by multi-chamber canister 12 in combination with bottom cover 40. For example, bottom cover 40 includes first molecular sieve chamber bottom wall 76, second molecular sieve chamber bottom wall 78, product tank bottom wall 80 and supply chamber bottom wall 82. The combination of the bottom walls and plenums enclose the respective chambers of multi-chamber canister 12.

The delivery of product gas to product chamber 24 from the respective molecular sieves is controlled in part by delivery system 84. Delivery system 84 includes first gas outlet port 86 defined within first molecular sieve chamber bottom wall 76 and second gas outlet port 88 defined within second molecular sieve chamber bottom wall 78. First gas outlet port 86 communicates with first delivery channel 90 and terminates at first internal gas outlet port 92 which is located within product chamber 24 for delivering concentrated oxygen from first molecular sieve chamber 16 to product chamber 24. Second gas outlet port 88 communicates with second delivery channel 94 and terminates at second internal outlet port 96 for delivering concentrated oxygen from second molecular sieve chamber 18 to product chamber 24. Dual check valve 98 overlies both first and second internal gas outlet ports 86 and 96. Both first and second internal gas outlet ports 86 and 96 will communicate with product chamber 24 when open. In the preferred embodiment, first and second internal gas outlet ports 86 and 96 and dual check valve 98 are located within supply chamber 24. Check valve retainer 100 maintains pressure on dual check valve 98 to close off first and second internal gas outlet ports 86 and 96 preventing a backflow of product gas to a respective molecular sieve ensuring that the product gas is delivered to product chamber 24.

During the purging cycle of each molecular sieve, purge control orifice 102 communicates pressurized gas from a molecular sieve which is undergoing a charging cycle to the other molecular sieve. Purge control orifice 102 extends through the abutting walls of first and second molecular sieve chambers 16 and 18. In the preferred embodiment, multi-chamber canister 12 is a single extrusion such that first and second molecular sieve chambers 16 and 18 share common wall 104, however, multi-chamber canister 12 can be comprised of an assembly of separate chambers integrated to form a multi-chamber assembly. In this situation, common wall 104 will comprise of separate molecular sieve chamber walls which abut. This design assists in maintaining an even temperature between the molecular sieves which enables the concentration of oxygen produced by each respective sieve to be approximately equal in concentration level.

Compressed air inlet 106 receives compressed air from a compressor and communicates the gas to supply chamber 14 through supply port 108 bypassing second molecular sieve chamber 18. As shown in FIG. 1 since the compressed air is received at the bottom of multi-chamber canister assembly 12, the compressed air must travel along the length of the canister to reach valve 32 for subsequent presentation to either first or second molecular sieve chambers 16 or 18. By requiring the compressed air to travel along the length of canister 12, the external wall of canister 12 functions as a heat exchanger for cooling the compressed air. Generally, air after compression is at a higher temperature than ambient. The effectiveness of the molecular sieves is increased with air at a cooler temperature. Accordingly, the cooling of the compressed air prior to entry into the molecular sieves enhances the efficiency of the pressure swing absorption system.

As shown in FIG. 4a, top cover 30 includes supply chamber top cavity 110 which encloses the top portion of supply chamber 24 of multi-chamber canister 12. Product supply port 112 communicates the concentrated gas to a patient through pressure regulator 36. Product chamber pressure sensor tap 114 enables the mounting of a pressure sensor for determining the pressure within product chamber 24.

Figure 6:
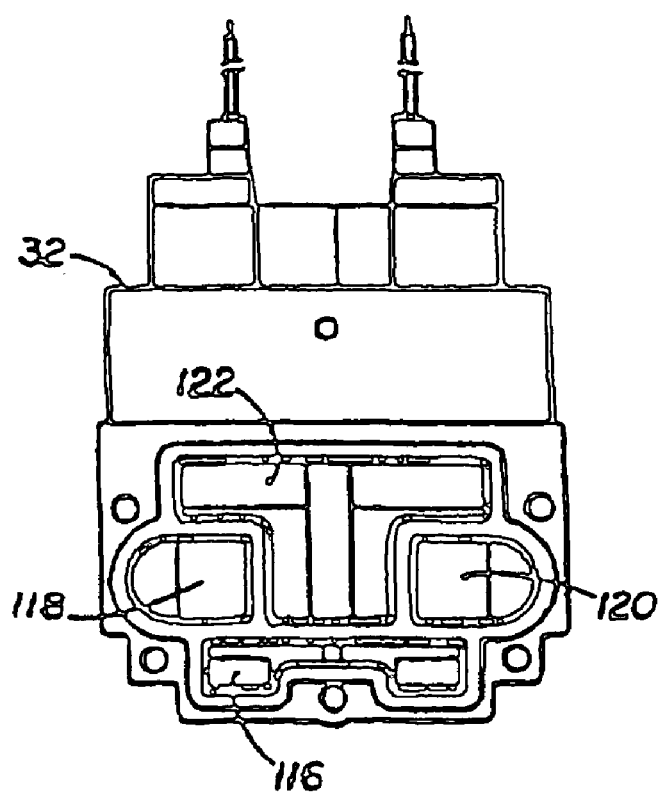
FIG. 6 is a perspective view of a valving system for communicating fluid flow within a multi-chamber canister for use in a pressure swing absorption system according to an embodiment of the present invention.
Figure 7:
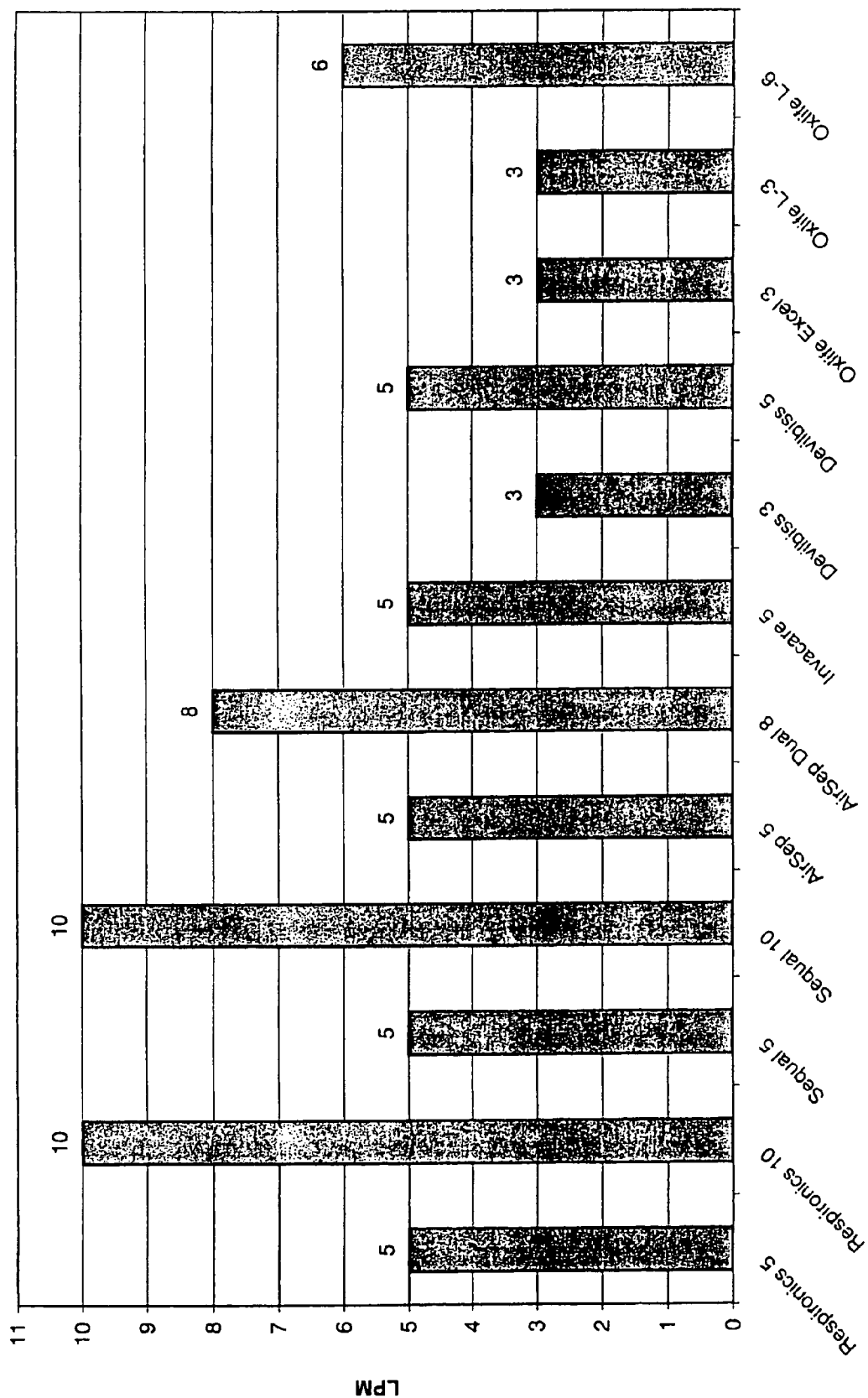
FIG. 7 is a graph of the O$_2$ output of the concentrators of TABLE 1.
Figure 8:
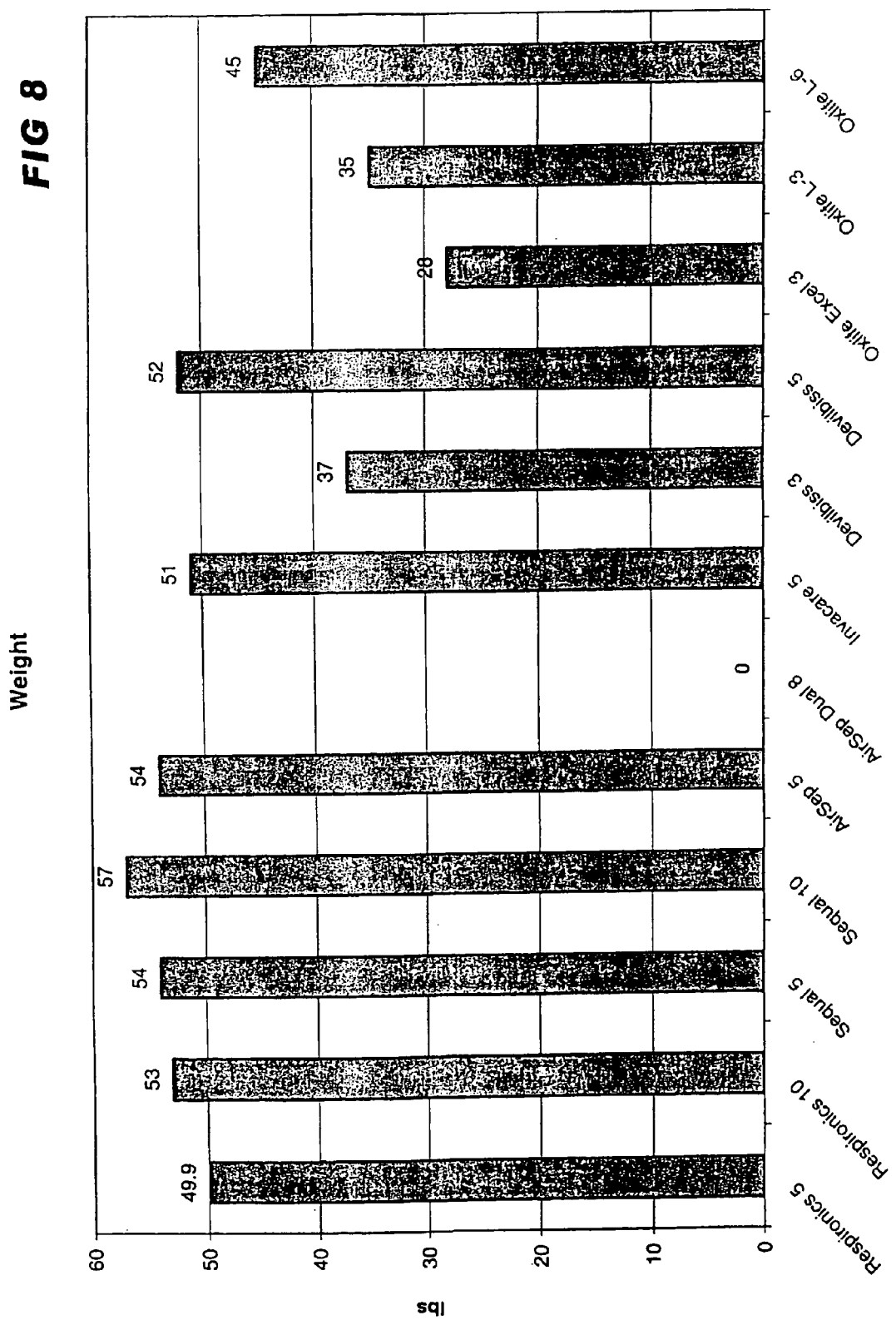
FIG. 8 is a graph of the weight of the concentrators of TABLE 1.
Figure 9:
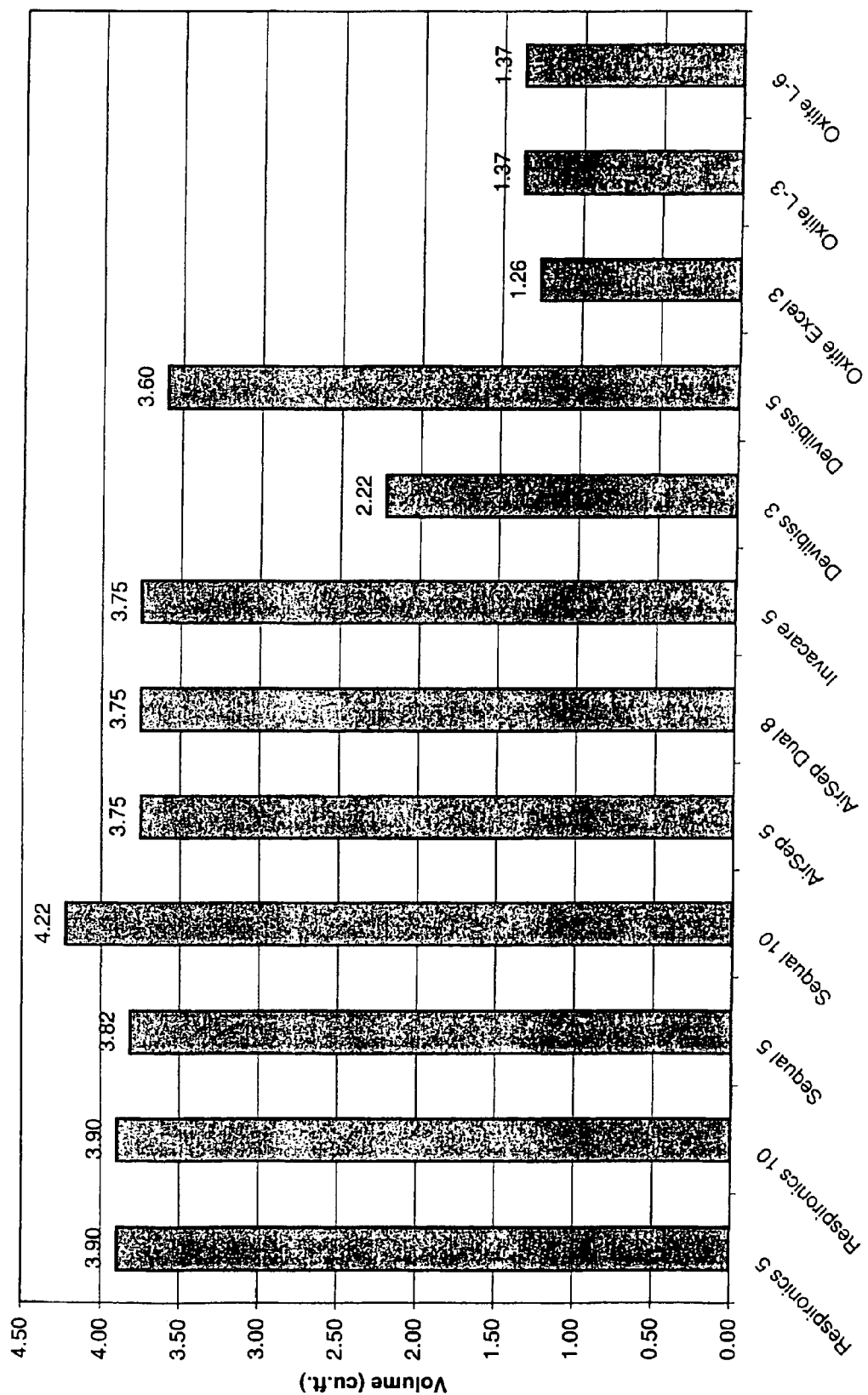
FIG. 9 is a graph of the size of the concentrators of TABLE 1.
Figure 10:
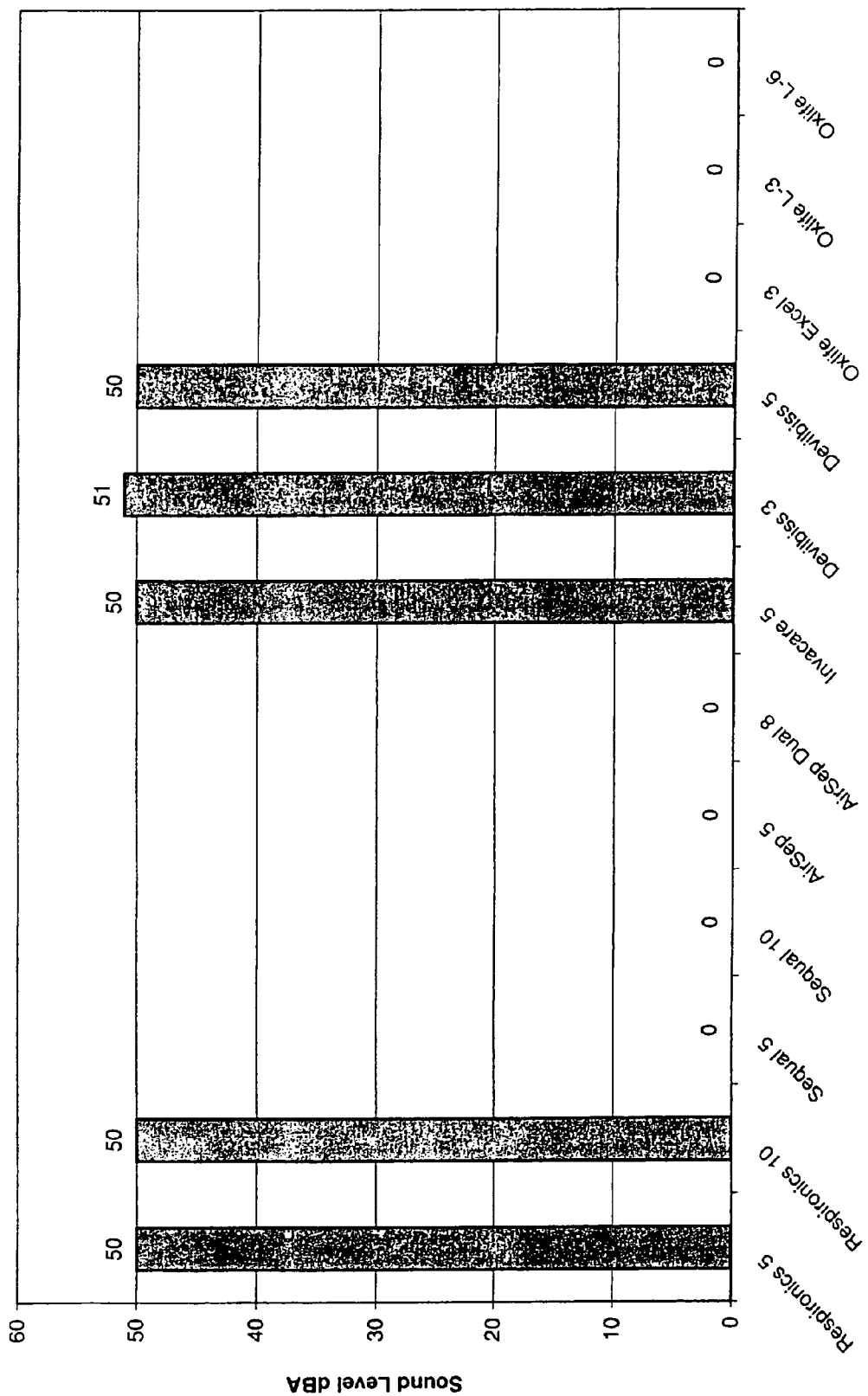
FIG. 10 is a graph of the sound levels of the concentrators of TABLE 1.
Figure 11:
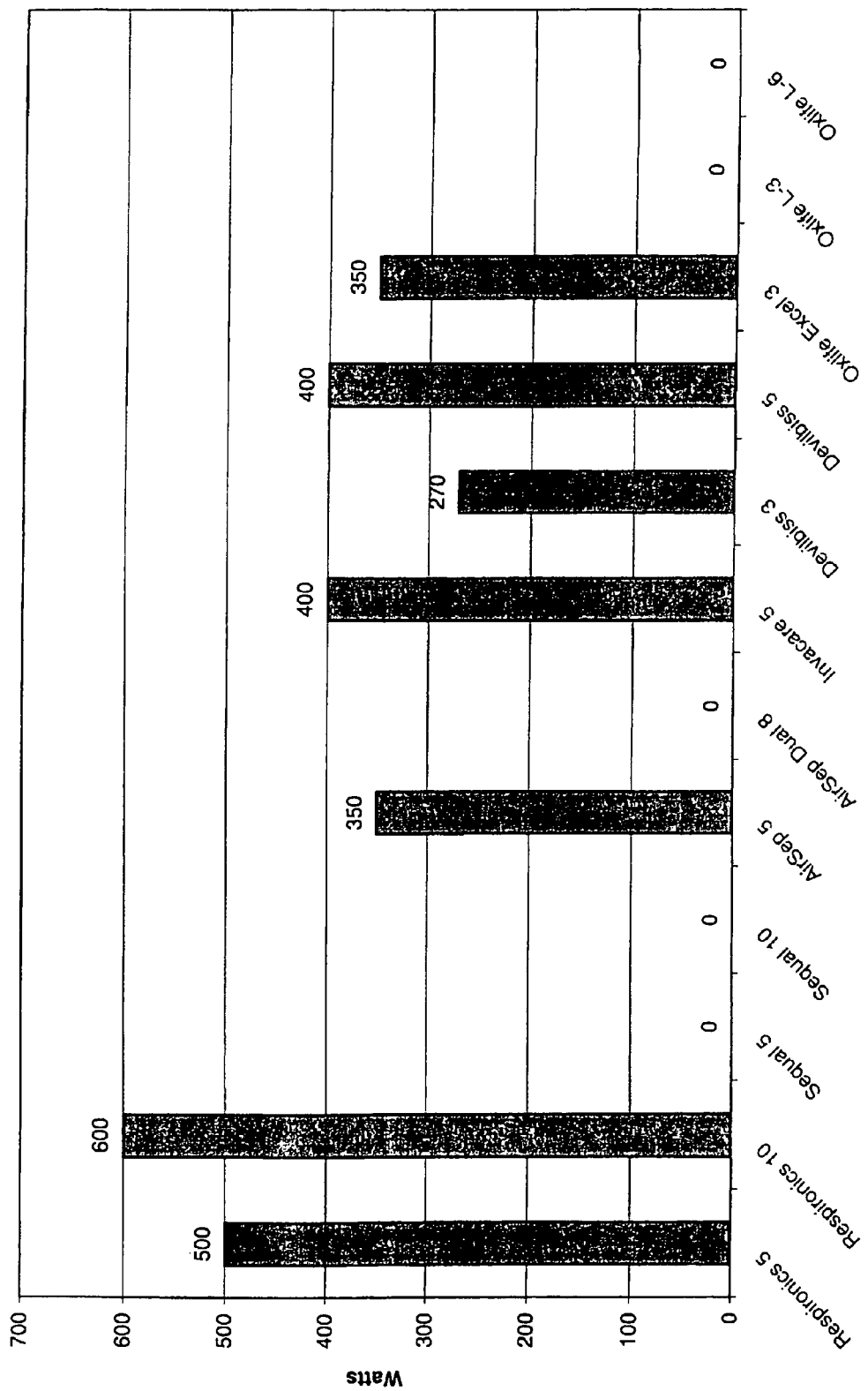
FIG. 11 is a graph of the power consumption of the concentrators of TABLE 1.

FIG. 6 illustrates valve 32. Valve 32 is carried by valve seat 44 for communicating the flow of fluid throughout the pressure swing absorption cycle. Valve inlet port 116 opens and closes for communicating compressed air from supply chamber 14 to molecular sieve chambers 16 and 18. First molecular sieve valve outlet 118 and second molecular sieve valve outlet 120 open and close to permit compressed air to enter the respective molecular sieves during operation of the pressure swing absorption cycle. Valve exhaust outlet 122 communicates with exhaust chamber 26 permitting purged gas to exit the respective molecular sieves and enter exhaust chamber 26 for venting through exhaust port 72. Valve 32 is controlled by a microprocessor and solenoids, not shown, for directing communication of fluid throughout the system.

When assembled as shown in FIG. 1, top and bottom covers 30 and 40 in combination with multi-chamber canister 12 define a fully integrated system wherein a supply chamber, product chamber, exhaust chamber and first and second molecular sieve chambers are enclosed within a general profile defined by multi-chamber canister 12. As previously mentioned, multi-chamber canister can be a single extrusion or a plurality of extrusions wherein the chambers are configured to be enclosed within separate extrusions and wherein the plurality of extrusions are assembled to define a configuration similar to that shown in FIG. 1.

In operation, air enters compressor 10 and is compressed resulting in the compressed air having a temperature higher than the ambient air. The compressed air enters multi-chamber canister 12 through bottom cover 40 and is presented to supply chamber 14. The compressed air is passed through supply chamber 14 to valve 32 for delivery to a respective molecular sieve chamber 16 or 18. Since valve 32 is located on opposite ends of multi-chamber canister 12, the compressed air travels along the length of multi-chamber canister 12 enabling multi-chamber canister 12 to act as a heat exchanger for cooling the compressed air prior to delivery to a respective molecular sieve. Valve 32 opens a respective molecular sieve chamber enabling the compressed air to enter the molecular sieve chamber. The molecular sieve material filters the nitrogen molecules from the air producing a concentration of oxygen. The concentrated oxygen in turn pressurizes a respective outlet port 86 or 88 which forces check valve retainer 100 to bend, opening up dual check valve 98 enabling the concentrated oxygen to enter product chamber 24, while simultaneously maintaining the other respective outlet port closed preventing a backflow of concentrated oxygen to flow into the other respective molecular sieve. The concentrated oxygen passes along the length of multi-chamber canister and exists through pressure regulator 36. Once again, the passage of the concentrated oxygen along the length of multi-chamber canister 12 enables multi-chamber canister 12 to act as a heat exchanger for cooling the concentrated oxygen prior to delivery to a patient.

Approximately one third of the concentrated oxygen enters product chamber 24 allowing the remaining two thirds to enter the other molecular sieve chamber through purge control orifice 102. Valve 32 simultaneously opens exhaust port 54 enabling nitrogen to be purged from the respective molecular sieve chamber and pass through exhaust port 54 in top cover 30 and enter into exhaust chamber 26 for subsequent venting at exhaust chamber outlet port 72 located in bottom cover 40. The cycle of charging and purging of the molecular sieves is further detailed in U.S. Pat. No. 5,183,483.

The present system thus provides a 10 LPM output in a unit having approximately the same size, weight, sound level and power consumption as a standard 5 LPM model. Preferable system characteristics for the present invention include an output of 10 LPM at 95% $O_2$, a sieve weight of 5.4 lbs., a unit weight of 53.5 lbs., a unit size of 26.8"×18.9"×13.3" (a volume of 6737 $in^3$, or 3.9 $ft^3$), a sound level at 1 m×1 m of 50 dBA, and a specific power of 600 W.

The present invention includes the provision of a high output concentrator that illustrates an advancement in technology when viewed under specific performance ratios, ratios unmet in the current art. The present invention has a specific unit weight per LPM<5.7 (preferably, for example, 53.5 lbs. per 10 LPM=5.35 lbs./LBM). The present invention has a specific sieve weight per LPM$\leq$1 (preferably, for example, 5.4 lbs. per 10 LPM=0.54 lbs./LBM). The present invention has a specific unit size per LPM<0.42 (preferably, for example, 3.9 $ft^3$ per 10 LPM=0.39 $ft^3$/LBM). The present invention has a specific sound level per LPM$\leq$10 (preferably, for example, 50 dBA per 10 LPM=5 dBA/LBM). Lastly, the present invention has a specific power level per LPM$\leq$120 (preferably, for example, 600 W per 10 LPM=60 W/LBM).

FIGS. 7-15 illustrate graphically many of the performance characteristics provided in TABLE 1.

The design of the present system, with its use of the improved compressor and adsorbent material over the prior art designs, not only provides a compact unit for the delivery of 10 LPM, but further delivers a reliable oxygen concentration of 93% or more at 10 LPM.

The present system further utilizes shorter cycle times that present 10 LPM systems. Cycle time refers to the time taken for the completion of one adsorption-desorption cycle, which in turn decides the productivity (amount of product produced per unit mass of the adsorbent per unit time) of the process. Hence, shorter cycle times translate into higher productivity.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. An absorption system for separating air into a concentrated gas component, said system comprising:
   an air supply;
   a compressor for receiving and compressing the air supply, providing a compressed air supply;
   molecular sieve material for separating the compressed air supply into a concentrated gas component; and
   an outlet delivering at least 10 liters per minute (LPM) of concentrated gas component from the molecular sieve material;
   wherein the system has total weight and the system has a specific total weight per LPM<5.7 lbs/LBM; and
   wherein the molecular sieve material has total weight and the system has a specific total molecular sieve material weight per LPM$\leq$1 lbs/LBM.

2. The system of claim 1, wherein the system comprises a pressure swing adsorption system.

3. The system of claim 1, wherein the molecular sieve material is a SILIPORITE® molecular sieve material.

4. The system of claim 3, wherein the molecular sieve material is housed in two molecular sieve chambers.

5. The system of claim 4, further comprising:
   a housing of a general length including a housing wall;
   a first molecular sieve chamber defined within said housing for receiving the molecular sieve material, the first molecular sieve chamber defined by a first molecular sieve chamber partition, wherein the first molecular sieve chamber partition and the housing wall define the first molecular sieve chamber;
   at least a second molecular sieve chamber defined within said housing for receiving the molecular sieve material, the second molecular sieve chamber defined by a second molecular sieve chamber partition, wherein the second molecular sieve chamber partition and the housing wall define the second molecular sieve chamber; and
   a supply chamber defined within the housing for receiving the compressed air supply and for communicating the compressed air supply to the first and the second molecular sieve chambers, the supply chamber defined by a supply chamber partition, wherein the supply chamber partition and the housing wall define the supply chamber, and wherein the supply chamber extends along a general length of the housing, the supply chamber including an air inlet for the air supply, the air inlet disposed a general distance apart from where the supply chamber fluidly communicates with either one of the first and the second molecular sieve chambers enabling the housing to act as a heat exchanger for cooling the air supply received from the air inlet.

* * * * *

UNITED STATES PATENT AND TRADEMARK OFFICE
CERTIFICATE OF CORRECTION

PATENT NO. : 7,780,769 B2  Page 1 of 1
APPLICATION NO. : 11/698682
DATED : August 24, 2010
INVENTOR(S) : Joseph T. Dolensky et al.

It is certified that error appears in the above-identified patent and that said Letters Patent is hereby corrected as shown below:

Claim 1, lines 12 and 15, please change LBM to LPM.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,780,769 B2 Page 1 of 1
APPLICATION NO. : 11/698682
DATED : August 24, 2010
INVENTOR(S) : Joseph T. Dolensky et al.

It is certified that error appears in the above-identified patent and that said Letters Patent is hereby corrected as shown below:

Column 10, lines 28 and 31
(Claim 1, lines 12 and 15), please change LBM to LPM.

This certificate supersedes the Certificate of Correction issued October 26, 2010.

Signed and Sealed this

Twenty-third Day of November, 2010

David J. Kappos
*Director of the United States Patent and Trademark Office*